(12) United States Patent
Auer et al.

(10) Patent No.: US 6,838,579 B2
(45) Date of Patent: Jan. 4, 2005

(54) UTILIZATION OF AN EXTRACTING AGENT AS ANTIFOAMING AGENT IN THE PRODUCTION OF ANHYDROUS FORMIC ACID

(75) Inventors: Heinz Auer, Neulussheim (DE); Bernd Bessling, Grosse Ille, MI (US); Hans Hammer, Mannheim (DE); Hans Hasse, Kaiserslautern (DE); Friedrich Sauer, Obersülzen (DE); Maximilian Vicari, Limburgerhof (DE); Gerhard Wagner, Ludwigshafen (DE); Till Adrian, Bobenheim-Roxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 8 days.

(21) Appl. No.: 10/181,460

(22) PCT Filed: Jan. 24, 2001

(86) PCT No.: PCT/EP01/00749

§ 371 (c)(1),
(2), (4) Date: Jul. 18, 2002

(87) PCT Pub. No.: WO01/55071

PCT Pub. Date: Aug. 2, 2001

(65) Prior Publication Data

US 2003/0009057 A1 Jan. 9, 2003

(30) Foreign Application Priority Data

Jan. 24, 2000 (DE) .......................................... 100 02 793

(51) Int. Cl.$^7$ ............................................. C07C 53/02
(52) U.S. Cl. ...................... 562/609; 562/606; 562/608
(58) Field of Search ........................................... 562/609

(56) References Cited

U.S. PATENT DOCUMENTS

| 4,326,073 A | 4/1982 | Wolf et al. .................. 562/609 |
| 4,551,208 A | * 11/1985 | Bott et al. .................... 203/60 |

FOREIGN PATENT DOCUMENTS

| CA | 1 238 919 | 7/1988 |
| EP | 0 017 866 | 10/1980 |
| EP | 0 156 309 | 10/1985 |

* cited by examiner

Primary Examiner—Joseph K. McKane
Assistant Examiner—Karl Puttlitz
(74) Attorney, Agent, or Firm—Keil & Weinkauf

(57) ABSTRACT

The invention relates to a process for obtaining anhydrous or substantially anhydrous formic acid in which, during the work-up, a compound of the general formula I (I)

Figure 1:
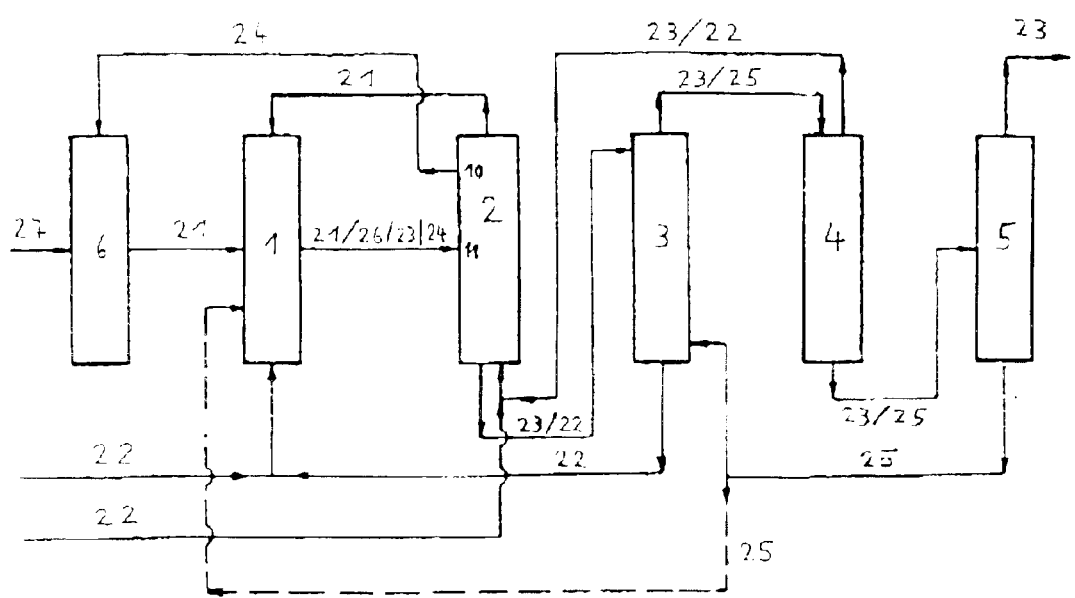

where the radicals R1 and R2 are alkyl, cycloalkyl, aryl or aralkyl groups, or R1 and R2 jointly, together with the N atom, form a heterocyclic 5- or 6-membered ring, and only one of the radicals is an aryl group, and where R3 is hydrogen or a C1–C4-alkyl group,
is employed simultaneously as extractant for formic acid and as antifoam for a distillation process.

6 Claims, 4 Drawing Sheets

UTILIZATION OF AN EXTRACTING AGENT AS ANTIFOAMING AGENT IN THE PRODUCTION OF ANHYDROUS FORMIC ACID

The present invention relates to an apparatus and a process for the preparation of anhydrous or substantially anhydrous formic acid, and to the use of the extractant employed in the work-up of formic acid.

TECHNICAL FIELD

"Ullmanns Encyklopädie der technischen Chemie" [Ullmann's Encyclopedia of Industrial Chemistry], 4th Edition, Volume 7, page 365, discloses that formic acid can be prepared by acidolysis of formamide using sulfuric acid. However, this process has the disadvantage that stoichiometric amounts of ammonium sulfate are obtained as an unavoidable product.

Another way of preparing formic acid consists in the hydrolysis of methyl formate, which is synthesized from methanol and carbon monoxide. This synthesis is based on the following equations:

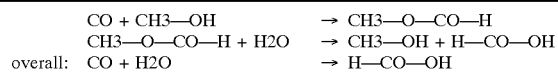

| | | |
|---|---|---|
| | CO + CH3—OH | → CH3—O—CO—H |
| | CH3—O—CO—H + H2O | → CH3—OH + H—CO—OH |
| overall: | CO + H2O | → H—CO—OH |

The hydrolysis of methyl formate described in "Ullmanns Encyklopädie der technischen Chemie" [Ullmann's Encyclopedia of Industrial Chemistry], 4th Edition, Volume 7, page 366

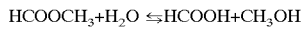

HCOOCH₃+H₂O ⇌ HCOOH+CH₃OH has the disadvantage of an unfavorable position of the hydrolysis equilibrium. A shift in the equilibrium by removing the desired process products by distillation is not possible since methyl formate (boiling point 32° C.) boils significantly lower than methanol (boiling point 65° C.) and formic acid (boiling point 101° C.). Anhydrous formic acid cannot easily be obtained from the resultant aqueous formic acid solution by distillation since it forms an azeotrope with water. The difficulty thus consists in obtaining anhydrous formic acid from the methyl formate hydrolysis mixture.

BACKGROUND ART

A process described in EP-B-0 017 866 which comprises steps a) to g) enables the preparation of anhydrous formic acid starting from methyl formate. Anhydrous formic acid is obtained here if a) methyl formate is subjected to hydrolysis,
b) methanol and excess methyl formate are distilled off from the resultant hydrolysis mixture,
c) the bottom product from the distillation (b), which comprises formic acid and water, is extracted in a liquid-liquid extraction with an extractant which principally takes up the formic acid,
d) the resultant extract phase, comprising formic acid, extractant and some of the water, is subjected to distillation,
e) the top product obtained in this distillation, which comprises water and some of the formic acid, is fed back into the lower part of the distillation column in step (b),
f) the bottom product from distillation step (d), which predominantly comprises extractant and formic acid, is separated into anhydrous formic acid and the extractant by distillation, and
g) the extractant leaving step (f) is fed back into the process.

In this process, it is particularly advantageous h) to carry out distillation steps (b) and (d) in a single column,
i) to introduce the water necessary for the hydrolysis in the form of steam into the lower part of the column provided for carrying out step (b),
k) to employ methyl formate and water in the hydrolysis (a) in a molar ratio of from 1:2 to 1:10, and/or
l) to employ, as extractant, a carboxamide of the general formula I

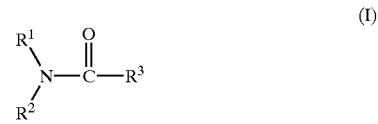

where the radicals R1 and R2 are alkyl, cycloalkyl, aryl or aralkyl groups, or R1 and R2 jointly, together with the N atom, form a hetero-cyclic 5- or 6-membered ring, and only one of the radicals is an aryl group, and where R3 is hydrogen or a C1–C4-alkyl group.

Steps (a) to (i) of the above-described process disclosed in EP-B-0 017 866 are explained in greater detail below.

Step (a)

The hydrolysis is usually carried out at a temperature in the range from 80 to 150° C.

Step (b)

The distillation of the hydrolysis mixture can in principle be carried out at any desired pressure, preferably from 0.5 to 2 bar. In general, working under atmospheric pressure is advisable. In this case, the temperature at the bottom of the column is about 110° C. and the temperature at the top of the column is from about 30 to 40° C. The hydrolysis mixture is advantageously added at a temperature in the range from 80 to 150° C., and the methanol is preferably removed in liquid form at a temperature of from 55 to 65° C. Satisfactory separation of the mixture into methyl formate and methanol on the one hand and aqueous formic acid on the other hand is possible even using a distillation column which has 25 theoretical plates (the theoretical number of plates is preferably from 35 to 45). Any design can be used for the column intended for step (b), but a sieve-plate or packed column is particularly recommended.

Step (c)

The liquid-liquid extraction of the formic acid from its aqueous solution by means of an extractant is preferably carried out at atmospheric pressure and a temperature of from 60 to 120° C., in particular from 70 to 90° C., in countercurrent. Depending on the type of extractant, extraction devices having from 1 to 12 theoretical separation stages are generally required. Suitable extraction devices for this purpose are in particular liquid-liquid extraction columns. In most cases, satisfactory results are achieved using from 4 to 6 theoretical separation stages.

The choice of extractant is not limited. Particularly suitable extractants are carboxamides of the general formula I given above. Extractants of this type are, in particular, N-di-n-butylformamide and in addition N-di-n-butylacetamide, N-methyl-N-2-heptylformamide, N-n- butyl-N-2-ethylhexylformamide, N-n-butyl-N-cyclohexylformamide and N-ethylformanilide, and mixtures of these compounds. Further suitable extractants are, inter alia, diisopropyl ether, methyl isobutyl ketone, ethyl acetate, tributyl phosphate and butanediol formate.

Step (d)

The extract phase is separated by distillation in an appropriate distillation device into a liquid phase, which generally comprises predominantly formic acid and extractant, and a vapor phase predominantly comprising water and small amounts of formic acid. This is an extractive distillation. The bottom temperature is preferably from 140 to 180° C. A satisfactory separation effect is generally achieved from 5 theoretical plates.

Step (e)

The formic acid/water mixture is generally recycled in vapor form.

Steps (f) and (g)

The distillation device (usually in the form of a column) for carrying out step (f) is advantageously operated under reduced pressure—from about 50 to 300 mbar and correspondingly low head temperatures—from about 30 to 60° C.

Step (h)

This variant of the process relates to steps (b) and (d). The distillation devices for carrying out steps (b) and (d) are arranged in an overall distillation device. The distillation devices here are generally in the form of columns.

Step (i)

In this step, water required for the hydrolysis is provided in the form of steam.

In the process described above, methyl formate is hydrolyzed in a hydrolysis reactor with a molar excess of water. The hydrolysis reaction is preferably carried out as a pure liquid-phase reaction at temperatures from 80 to 150° C. In order to be able to achieve these temperatures of the reaction mixture, the hydrolysis must be carried out at superatmospheric pressure—at atmospheric pressure, the reaction mixture would have a boiling point below the temperature range indicated above. In the subsequent step, the hydrolysis mixture from the hydrolysis reactor is passed into a distillation column for distillative separation. A lower pressure prevails in the latter than comparatively in the hydrolysis reactor. On introducing the hydrolysis mixture into the distillation column, the hydrolysis mixture is thus decompressed suddenly (abrupt drop in pressure). The consequence is vigorous foaming of the hydrolysis mixture introduced into the distillation column. The foaming has highly adverse effects on the separation performance of the distillation internals of the distillation column, since the foaming is associated with intensive back-mixing of the internal gas and liquid streams in the distillation column, which preferably run in countercurrent. In addition, the fluid-dynamic working range is greatly restricted by the foaming, since the foam causes an unacceptable pressure loss in the column. In order to prevent the foaming, a commercially available antifoam can be added to the distillation column, above the feed point for the hydrolysis mixture. This reduces or greatly restricts the foaming, so that the adverse consequences of foaming described above are excluded. Examples of suitable antifoams which can be employed are silicone oils. The costs of the antifoams have an adverse effect on the economic efficiency of the process. Secondly, the addition of the commercially available antifoams is accompanied by introduction of foreign substances into the process, which generally have an adverse effect on the product quality. Since the degradation products of the antifoams must be eliminated from the process, considerable disposal costs arise in the treatment of the corresponding waste water.

DISCLOSURE OF THE INVENTION

It is an object of the present invention to provide a process in which foaming is prevented without high costs and an adverse effect on product quality occurring. A further aim is to minimize the disposal costs for the antifoam. The process should be simple and practical to carry out.

We have found that this object is achieved by a process for obtaining anhydrous or substantially anhydrous formic acid in which i) methyl formate is subjected to hydrolysis, ii) methanol and excess methyl formate are distilled off from the resultant hydrolysis mixture, iii) the bottom product from distillation ii), comprising formic acid and water, is extracted in a liquid-liquid extraction with an extractant which principally takes up the formic acid, and the extractant employed here is a carboxamide of the general formula I where the radicals R1 and R2 are alkyl, cycloalkyl, aryl or aralkyl

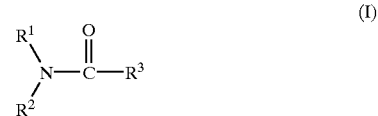

groups, or R1 and R2 jointly, together with the N atom, form a heterocyclic 5- or 6-membered ring, and only one of the radicals is an aryl group, and where R3 is hydrogen or a C1–C4-alkyl group, iv) the resultant extract phase, comprising formic acid, extractant and some of the water, is subjected to distillation, v) the top product obtained in this distillation, which comprises water and some of the formic acid, is fed back into the lower part of the distillation device in step ii), vi) the bottom product from distillation step iv), which comprises predominantly extractant and formic acid, is separated by distillation into anhydrous or substantially anhydrous formic acid and the extractant, and vii) the extractant leaving step vi) is fed back into the process, which comprises removing a sub-stream of the extractant employed from the process and feeding it to the distillation device provided for carrying out step ii), with the corresponding feed point for the sub-stream of the extractant in the distillation device being above the feed point of the hydrolysis mixture and below the removal point of methanol.

For the purposes of the present invention, the term "substantially anhydrous formic acid" is taken to mean formic acid which contains a maximum of 30%, preferably a maximum of 15%, of water.

The extractant introduced into the distillation device for carrying out step ii) prevents foaming. All suitable extractants of the general formula I boil higher than the components of the hydrolysis mixture (methyl formate, water, methanol and formic acid). The extractant introduced into the distillation column for carrying out step ii) thus flows out of the distillation column in liquid form and, together with the aqueous formic acid fed into the extractor, re-enters the extractant circuit. The advantages of the process according to the invention are clear. It is no longer necessary to employ an expensive additional antifoam which subsequently has to be removed from the process again. Costs for purchasing an antifoam and for waste-water treatment which would be associated with the introduction of an initial antifoam can thus be saved. It is basically advantageous if the introduction of foreign substances can be avoided in the process. The extractant as antifoam is thus a component which is already present in the process anyway—the introduction of an additional antifoam is avoided.

Preferred extractants are N,N-di-n-butylformamide, N,N-di-n-butylacetamide, N-methyl-N-2-heptylformamide, N-n-butyl-N-2-ethylhexylformamide, N-n-butyl-N-cyclohexylformamide and/or N-ethylformanilide.

MODE(S) FOR CARRYING OUT THE INVENTION

In a preferred embodiment of the invention, the sub-stream of the extractant employed which is fed to the distillation device for carrying out step ii) is taken from the extractant leaving step vi). In principle, however, the extractant for the provision of the sub-stream can be taken from any desired point of the process. Extractants which can be employed are also mixtures which comprise the various extractants according to the invention. Besides extractant, the extractant used as antifoam can also contain other components, in particular formic acid, water, methanol and/or methyl formate. The introduction of additional antifoams which are not in accordance with the invention is in principle possible.

In general, distillation steps ii) and iv) are carried out in a single distillation device.

The invention also relates to the use of a carboxamide of the general formula I

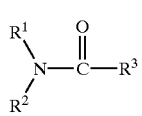

where the radicals R1 and R2 are alkyl, cycloalkyl, aryl or aralkyl groups, or R1 and R2 jointly, together with the N atom, form a heterocyclic 5- or 6-membered ring, and only one of the radicals is an aryl group, and where R3 is hydrogen, in the above-described process as antifoam in the distillative separation of the hydrolysis mixture comprising methyl formate, water, formic acid and methanol, and as extractant for the liquid-liquid extraction of the formic acid.

The invention also relates to a device for carrying out the process explained above, which comprises α) a synthesis reactor, β) a hydrolysis reactor, χ) a distillation device for carrying out step ii), δ) a distillation device for carrying out step iv), ε) an extraction device, φ) a distillation device for carrying out step vi), and γ) a connecting line for feeding a sub-stream of the extractant into the distillation column provided for carrying out step ii).

The term "synthesis reactor" is taken to mean a device in which on the one hand the synthesis of methyl formate is carried out (usually in a corresponding reactor) and, if desired, on the other hand separation of the resultant synthesis mixture is carried out (usually in a distillation device downstream of the reactor). The hydrolysis reactor employed can also be any desired reactor which is suitable for the hydrolysis of methyl formate. The distillation devices are generally in the form of columns. The extractant device employed is preferably a liquid-liquid extraction column. The connecting line for feeding a sub-stream of the extractant into the distillation column proposed for carrying out step ii) is generally in the form of a tube arranged between the distillation device 2 for carrying out step ii) and an outlet tube for extractant leaving the distillation device for carrying out step iv).

In a preferred embodiment of the invention, the distillation device for carrying out step ii) and the distillation device for carrying out step iv) are arranged in a single distillation device. The latter is generally in the form of a column.

Figure 2:
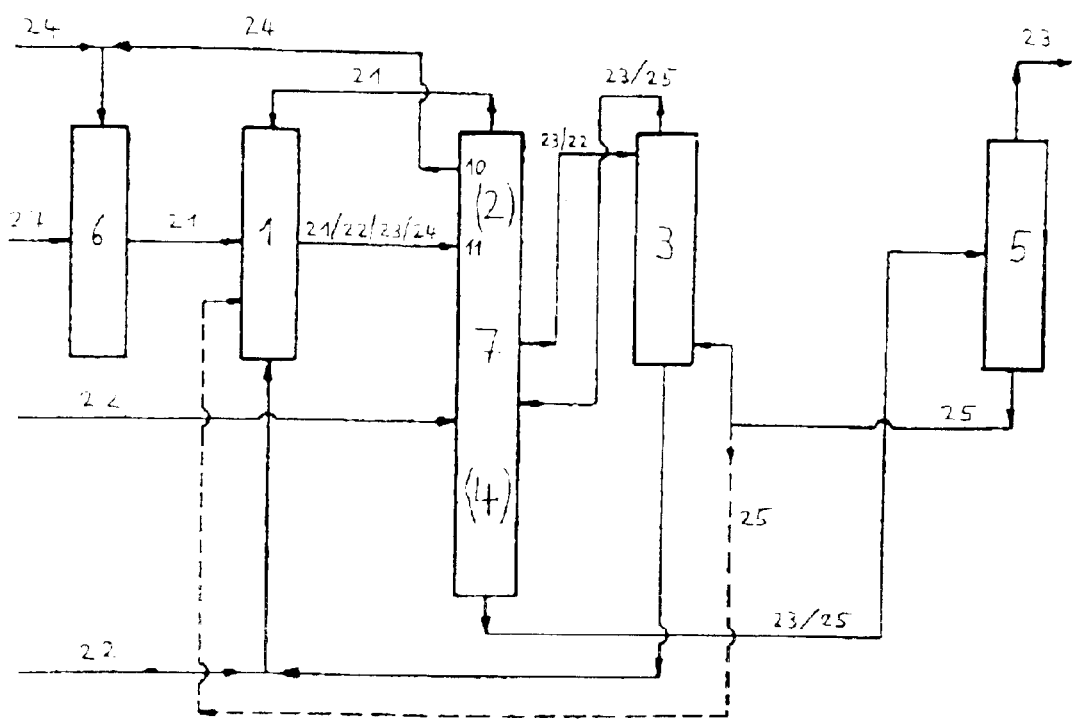
Figure 3:
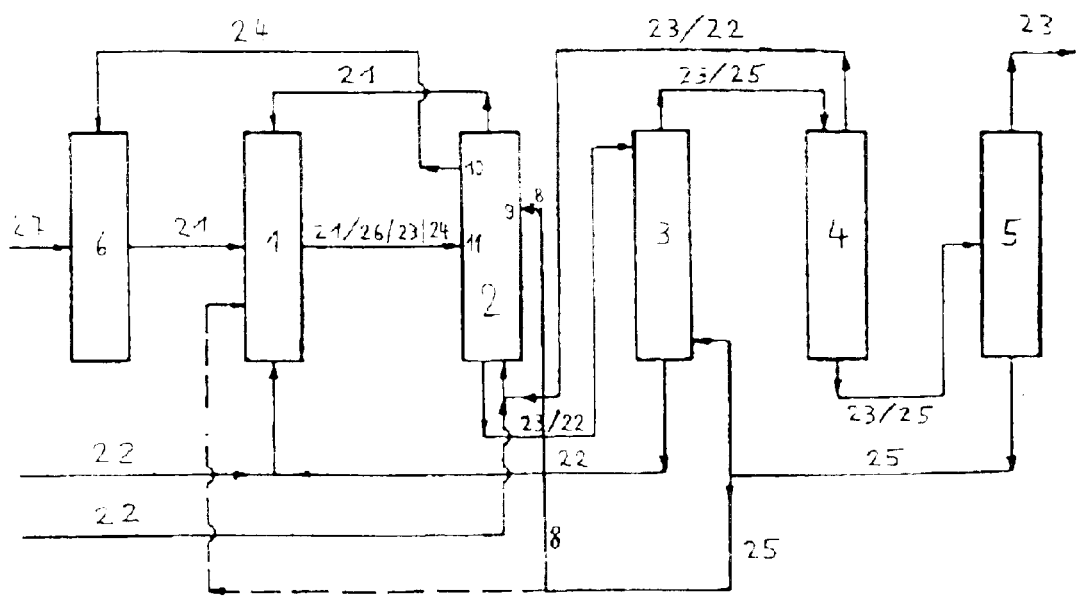
Figure 4:
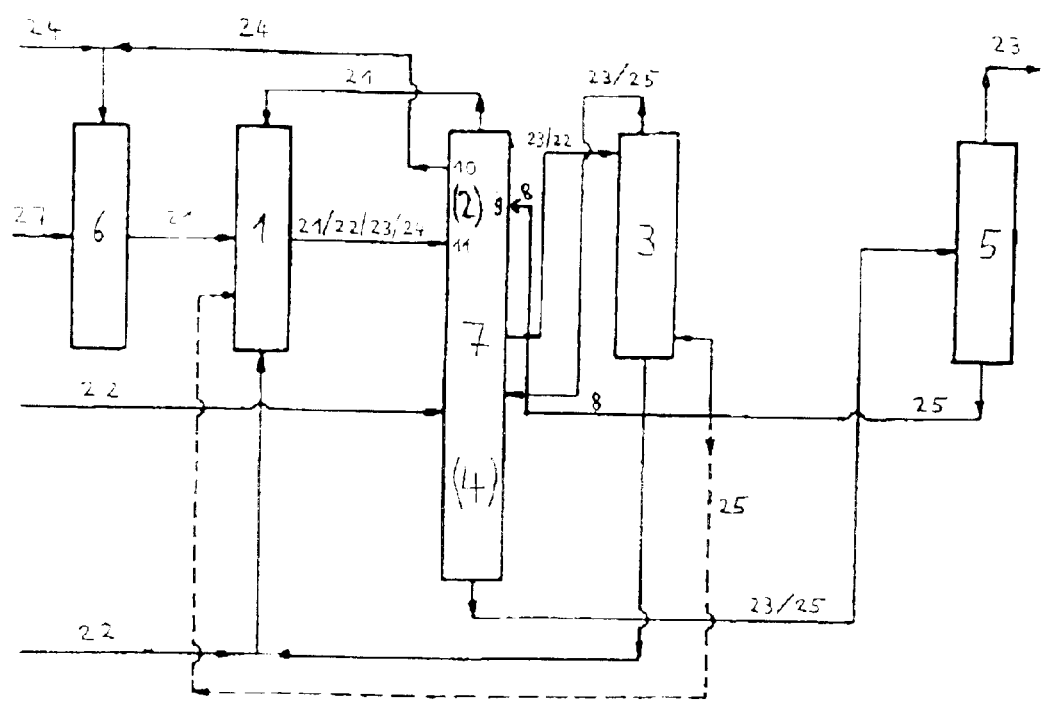

The attached drawing shows in FIG. 1 and FIG. 2 diagrams of plants for the preparation of anhydrous or substantially anhydrous formic acid in accordance with the prior art, and in FIG. 3 and FIG. 4 diagrams of plants for the preparation of anhydrous or substantially anhydrous formic acid in accordance with the process according to the invention.

The reference numerals entered above, below or alongside the connecting lines or arrows correspond to the components which generally form the major component of the corresponding stream. Since the composition in the streams can vary, these numbers are merely intended as a guide value. 21 here denotes methyl formate, 22 denotes water, 23 denotes formic acid, 24 denotes methanol, 25 denotes extractant and 27 denotes carbon monoxide.

The plants shown diagrammatically in FIG. 1 and FIG. 2 for carrying out the process in accordance with the prior art and the plants shown diagrammatically in FIG. 3 and FIG. 4 for carrying out the process according to the invention have the common feature that they comprise a synthesis reactor 6, a hydrolysis reactor 1, a distillation device 2 for carrying out step ii), a distillation device 4 for carrying out step iv), an extraction device 3 and a distillation device for carrying out step vi). The distillation devices 2 and 4 may be arranged in a common distillation device 7.

In contrast to the prior-art plants shown in FIG. 1 and FIG. 2, the plants shown in FIG. 3 and FIG. 4 for carrying out the process according to the invention comprise a connecting line 8 for feeding a sub-stream of the extractant into the distillation column 2 proposed for carrying out step iv). This sub-stream of extractant is taken from the extractant stream leaving the distillation device 5, and is advantageously cooled. The connecting line 8 runs into the distillation device 2 for carrying out step ii) at the feed point 9. This feed point 9 for the sub-stream of the extractant is arranged in the distillation device above the feed point 11 for the hydrolysis mixture and below the removal point 10 for methanol. In general, the feed point 9 for the extractant is located from 2 to 40 theoretical stages, in particular from 5 to 20 theoretical separation stages, above the feed point 11 for the hydrolysis mixture.

The invention will be explained in greater detail below with reference to a working example.

EXAMPLE

The illustrative experiment according to the invention is carried out in a plant which is shown diagrammatically in FIG. 4. 5.3 kg/h of aqueous formic acid are prepared continuously. The distillation device 7 used, which is in the form of a pilot-plant column, has a diameter of 100 mm and is fitted with 100 bubble-cap plates. The corresponding reactor discharge is 20 kg/h. The hydrolysis mixture is introduced at the forty-fifth plate, while the antifoam is introduced at the sixty-fifth plate. The column is operated under atmospheric pressure. The extractant employed is N,N-di-n-butylformamide. A 200 g/h extractant stream is fed in 20 plates above the feed 11 for the hydrolysis mixture. This enables foaming to be completely suppressed. This measure enables the plates above the feed point 11 for the hydrolysis mixture to achieve the usual efficiency on addition of antifoams of 0.7 theoretical separation stages per practical plate. The pressure loss is 2 mbar per plate.

For Comparison:

Without addition of an antifoam, vigorous foaming occurs in the distillation device 2 above the feed point of the hydrolysis mixture 11. The foaming reduces the plate efficiency of the foam-filled plates to 0.2 theoretical separation stages per practical plate. The pressure loss is 3.5 mbar per plate.

The above experiment shows that the extractant employed is suitable as antifoam in the process according to the invention.

We claim:

1. A process for obtaining anhydrous or substantially anhydrous formic acid, in which
   i) methyl formate is subjected to hydrolysis,
   ii) methanol and excess methyl formate are distilled off from the resultant hydrolysis mixture,
   iii) the bottom product from distillation (ii), comprising formic acid and water, is extracted in a liquid—liquid extraction with an extractant which principally takes up the formic acid, and the extractant employed here is a carboxamide of the general formula I

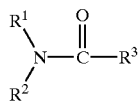

(I)

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group,
   iv) the resultant extract phase, comprising formic acid, extractant and some water, is subjected to distillation,
   v) the top product obtained in this distillation, which comprises water and some of the formic acid, is fed back into the lower part of the distillation device in step ii),
   vi) the bottom product from distillation step iv), which comprises predominantly extractant and formic acid, is separated by distillation into anhydrous or substantially anhydrous formic acid and the extractant, and
   vii) the extractant leaving step vi) is fed back into the process, which comprises removing a sub-stream of the extractant employed from the process and feeding it to the distillation device provided for carrying out step ii), with the corresponding feed point for the sub-stream of the extractant in the distillation device being above the feed point of the hydrolysis mixture and below the removal point of methanol.

2. The process claimed in claim 1, wherein the extractant employed is at least one compound selected from the group consisting of N,N-di-n-butylformamide, N,N-di-n-butylacetamide, N-methyl-N-2-heptylformamide, N-n-butyl-N-2-ethylhexylformamide, N-n-butyl-N-cyclohexylformamide and N-ethylformanilide.

3. The process claimed in claim 1, wherein the sub-stream of the extractant employed is taken from the extractant leaving step vi).

4. The process claimed in claim 1, wherein distillation steps ii) and iv) are carried out in a single distillation device.

5. A method for preventing foam in a distillation of a hydrolysis mixture comprising methyl formate, water, formic acid and methanol in a distillation device in a process according to claim 1 which comprises feeding to the distillation device a separate stream consisting essentially of a carboxyamide of formula I

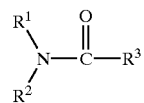

(I)

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group.

6. The process claimed in claim 1, wherein the sub-stream of extractant is cooled before being fed to the distillation device provided for carrying out step ii).

* * * * *